United States Patent [19]

Liang et al.

[11] Patent Number: 5,534,406
[45] Date of Patent: Jul. 9, 1996

[54] METHOD OF DETECTING ANTIGENIC NUCLEIC ACID-CONTAINING MACROMOLECULAR ENTITIES

[75] Inventors: Tsanyang Liang, Brookline; Jack R. Wands, Waban, both of Mass.

[73] Assignee: The General Hospital Corporation, Boston, Mass.

[21] Appl. No.: 204,885

[22] Filed: Mar. 2, 1994

Related U.S. Application Data

[60] Continuation of Ser. No. 701,148, May 17, 1991, which is a division of Ser. No. 262,347, Oct. 25, 1988, Pat. No. 5,077,192.

[51] Int. Cl.[6] .................................................. C12Q 1/70
[52] U.S. Cl. ............................. 435/5; 435/6; 435/7.1; 435/7.2; 436/541; 436/519; 530/413
[58] Field of Search ........................... 435/5, 6, 7.1, 7.2; 436/541, 519; 530/413

[56] References Cited

U.S. PATENT DOCUMENTS

| 4,358,535 | 11/1982 | Falkow et al. | 435/5 |
|---|---|---|---|
| 4,677,055 | 6/1987 | Dodin et al. | 435/7 |
| 4,683,195 | 7/1987 | Mullis et al. | 435/6 |
| 5,077,192 | 12/1991 | Liang et al. | 435/5 |

FOREIGN PATENT DOCUMENTS

| 0145356 | 11/1984 | European Pat. Off. | 1/68 |

OTHER PUBLICATIONS

Promega catalog page Jun. 2 "LambdaSorb™".

*Primary Examiner*—Christine M. Nucker
*Assistant Examiner*—Jeffrey Stucker
*Attorney, Agent, or Firm*—Sterne, Kessler, Goldstein & Fox

[57] ABSTRACT

A method for the detection of nucleic acid-containing moieties is described which combines affinity capture of the moiety with detection and identification of the moiety's nucleic acid.

3 Claims, 4 Drawing Sheets

METHOD OF DETECTING ANTIGENIC NUCLEIC ACID-CONTAINING MACROMOLECULAR ENTITIES

RIGHTS OF THE FEDERAL GOVERNMENT

The research underlying this patent application was supported by National Institutes of Health Grant CA35711; the Government has certain rights in this invention.

RELATED APPLICATION

This application is a continuation of application Ser. No. 07/701,148, filed May 17, 1991, which is a divisional of U. S. patent application Ser. No. 07/262,347which was filed on Oct. 25, 1988, U. S. Pat. No. 5,077,192, issued Dec. 31, 1991.

FIELD OF THE INVENTION

The invention relates to a method for the detection of low levels of moieties such as organisms and antigenic, nucleic add-containing, macromolecular entities. In a specific embodiment, the invention relates to a method for the detection of hepatitis virus which combines immunological capture of viral particles with amplification and identification of viral nucleic acid sequences.

BACKGROUND OF THE INVENTION

The rapid detection and identification of medically important organisms and macromolecular entities such as bacteria, viruses, malignant cells and the like is of critical importance in establishing diagnoses, treating patients, tracing the sources of infections, detecting biological contamination, and routinely screening and monitoring blood, other tissues and food so that public health might not be compromised.

The ability to detect and identify pathogenic organisms and macromolecular entities is limited by the sensitivity and rapidity of the detection system. In addition, identification of pathogenic organisms in blood or tissue samples poses special problems; not only is the availability of sample limited but the concentration of the pathogenic organism in that sample is often very low.

Techniques based on molecular methods of detection such as nucleic acid hybridization, restriction enzyme analysis, Southern analysis, Northern analysis, Western analysis and immunoassay have not overcome the problem of detecting low levels of pathogenic entities in dilute conditions. In many cases it is necessary to first incubate samples suspected of containing a pathogenic organism so as to enrich and increase the number of organisms to identifiable levels before detection and identification are possible (Andrews, W. H., Food Tech. 39:77–82 (1985)). However, growth and enrichment steps are extremely time-consuming in situations where time is of the essence to establish the presence or identification of an infectious organism.

In addition, growth requirements for some organisms are very complex and false negatives are a concern. Lack of growth of a bacterium may only indicate that the growth conditions weren't favorable, or that other, nonpathogenic bacteria in the sample grew faster than the organism in question and successfully "competed it out".

Methods for the detection and identification of pathogenic entities such as viruses are even more complex than those for entities like bacteria. More commonly, they depend on the acute and convalescent measurement of a serologic or antibody response to the infectious agent. These measurements are often time-consuming. They often depend on the identification and use of a suitable cell line which the virus can infect and in which the virus can replicate. They may also depend on the identification of an animal host which the virus can infect and in which the virus will induce diagnostic, serological symptoms.

Thus the identification of a pathogenic organism in blood and tissue samples may be missed even though the organism is present in the sample at levels infectious to humans.

Specific affinity reagents such as high affinity monoclonal antibodies have, in some cases, made it possible to confirm the presence, in blood or tissue samples, of organisms known or suspected of being infectious or otherwise pathogenic. For example, high affinity monoclonal antibodies directed to the hepatitis B surface antigen ($HB_sAg$) have been developed (Wands, J. R., et al., *Gastroenterology* 80:225–232 (1981)). These antibodies have successfully identified low levels of hepatitis B virus or its variants in the blood and tissues of some patients with acute and chronic liver disease but without known serologic markers of recent or past hepatitis B infection and also in some "healthy" individuals without clinical symptoms (Ben-Porath, E. et al., *Progress in Liver Diseases* 8:347–366 (1986); Ben-Porath, E. et al., *J. Clin. Invest.* 76:1338–1347 (1985)).

However, studies using monoclonal antibodies have been limited because it has been impossible to further characterize or study the molecular identity of the virus or variant in these patients. Levels of the virus, although detectable with the monoclonal antibody, are often too low for cloning, sequencing and other methods of viral characterization (See, e.g., Dienstag, J. L. et al., in *Harrison's Principles of Internal Medicine*, R. G. Petersdoff et al., eds., tenth edition, 1983, pp.1789–1801, McGraw-Hill, New York, incorporated herein by reference).

Current methods of identifying hepatitis B virus or its variants have depended on in vitro culture of the virus, radioimmunoassay, or genomic type identification after extraction of the vital DNA or RNA. However, these techniques do not always provide the necessary sensitivity for medical screening, diagnostic or treatment purposes (Id.). In addition, methods like radioimmunoassay may non-specifically detect the presence of viral antigens without providing information about the specific subtype.

The polymerase chain reaction (PCR) is a powerful technique for the amplification of specific DNA sequences (Cohen, S. N., U.S. Pat. No. 4,293,652; Erlich, H. A. et al., EP 258,017; Mullis, K. B., EP 201,184; Mullis et al., EP 200,362; Saiki, R. K., et al., *Science* 239:487–491 (1988); Mullis, K. B. et al., *Meth. Enzymol.* 155:335–350 (1987); Scharf, R. K., et al., Science 233:1076–1079 (1986) and Saiki, R. K., et al., *Science* 230:1350–1354 (1985)).

PCR has the ability to amplify a DNA sequence several orders of magnitude in a few hours, and has been used for: the detection of low levels of viral sequences (Kwok, S. et al., *J. Virol.* 61:1690–1694 (1987)), including hepatitis B (Kaneko, S., et al., *Hepatology* 8:1222 (1988)); cloning of low-abundant DNA sequences (Lee, M.S., et al., *Science* 237:175–178 (1987) ); the detection of malignant cells with chromosomal rearrangements (Lee, M.S., et al., *Science* 237:175–178 (1987)); the amplification of somatic mutational activation of cellular oncogenes in human tumors (Almoguera, C., et al., *Cell* 53:549–554 (1988)); and the detection and identification of individual DNA genotype in clinical and forensic samples (Marx, J. L., *Science* 240:1408–1410 (1988)), and haplotype (Li, H. et al., *Nature* 33.5:414–417 (1988)). The use of the PCR as a DNA diagnostic technique has been recently reviewed (Landegren, U., et al., *Science* 242:229–237 (1988), incorporated herein by reference).

PCR is based on the use of oligonucleotide primers, complementary to sequences flanking a particular region of interest, for primer-directed DNA synthesis in opposite and overlapping directions. With repeated cycles of high-temperature template denaturation, oligonucleotide primer reannealing, and polymerase-mediated extension, DNA sequences can be faithfully amplified several hundred-thousand fold. The amplified sequences are remarkably accurate so one can reliably determine the nucleotide sequences immediately after PCR.

In theory, only one copy of the target gene need be present in a sample for PCR to adequately target and amplify it. For example, PCR amplification technique has been used to analyze the DNA in an individual diploid cell and a single sperm (Li, H., et al., *Science* 335: 414–417 (1988)). Ou, C. Y., et al., have suggested the use of PCR for the detection of HIV-1 virus in DNA from peripheral blood mononuclear cells (*Science* 239:295–297 (1988)).

However, use of PCR is not immediately applicable to all samples. For example, it is not possible to directly test blood or serum using PCR because serum contains many inhibitors of this technique. Studies utilizing PCR to investigate blood cells have had to first isolate DNA from the cells by phenol or other similar, suitable techniques known in the art for isolation and concentration of DNA. This results in a large loss of sensitivity.

Thus, there remains a need for methodology, applicable to serum and other biological samples, for the rapid identification of low levels of pathological entities. Such methodology would not require DNA isolation or prolonged incubation in vitro, would be sensitive enough to detect the presence of extremely dilute levels of organisms and macromolecular entities in a sample and would permit the cloning and genetic analysis of the pathological entity. Such methodology would still be technically simple enough to be embodied as a kit, and amenable for use as a routine screening method.

SUMMARY OF THE INVENTION

The present invention provides a method for the detection and identification of moieties such as antigenic, nucleic acid-containing organisms and macromolecular entities which comprises trapping, concentrating and sequestering the organism or macromolecular entity with an affinity capture reagent and then detecting or identifying said moieties using amplified nucleic acid sequences specific to those moieties.

As an illustration, the present invention provides a method for the detection and identification of hepatitis B virus and its variants which is approximately 1000-fold more sensitive than immunoanalysis alone. It comprises immunological capture and concentration of hepatitis B virus particles using high affinity monoclonal antibodies and amplification of specific, hepatitis B target genomic loci using PCR.

BRIEF DESCRIPTION OF THE DRAWINGS

FIG. 1 is a Southern analysis which shows the sensitivity of PCR after 25 cycles for the detection of hepatitis B virus DNA.

DETAILED DESCRIPTION OF THE INVENTION

Figure 1A:
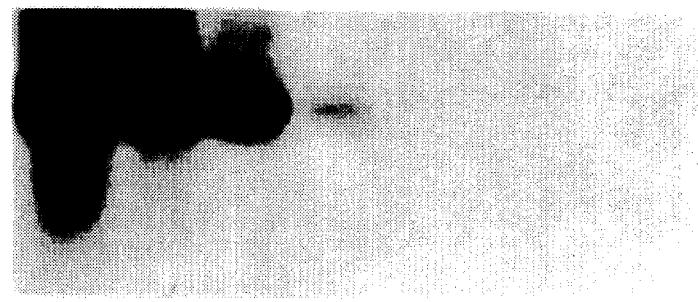
FIGS. 1A and 1B are one hour and three day exposures, respectively, of the same autoradiograph. The picograms (pg) of virus detected by the signal is placed above each lane.

The invention provides a sensitive and specific method for the detection and identification of nucleic acid-containing moieties which comprises high-affinity capture of such moieties and analysis of macromolecular entity-specific nucleic acid in such moieties.

This method is capable of detecting and identifying low levels of biological organisms such as bacteria, viruses, parasites, and the like, from serum and other biological sources.

For example, this method is capable of concentrating, detecting and identifying extremely low levels of hepatitis B virus or its variants in serum.

In detail, the invention provides a method of isolating and identifying nucleic acid-containing moieties, such as organisms and macromolecular entities by, first, isolating, concentrating, and sequestering the moiety from the sample milieu. The isolation, concentration, and sequestration is achieved with an affinity reagent such as a high affinity monoclonal antibody. The trapped moiety may then be lysed, its DNA denatured, and defined regions of genomic or other nucleic acid sequences associated with the entity detected, identified or otherwise characterized using amplified nucleic acid sequences specific to a known DNA.

Consequently, the invention embraces any method which uses a combination of affinity capture and nucleic acid analysis to extract, concentrate, amplify, characterize and/or identify nucleic acid-containing organisms or macromolecular entities.

DESCRIPTION OF THE PREFERRED EMBODIMENTS

The invention is originally based on the inventors' surprising discovery that unprecedented levels of sensitivity and speed of detection of hepatitis B virus or variants are achieved when solid phase, high affinity monoclonal antibodies to hepatitis B surface antigens are used to extract, concentrate, immobilize and sequester hepatitis B particles from serum, in a manner which allows extraction and isolation of the virus away from nondesirable components present in serum, and in a manner which allows recovery of the virus and subsequent analysis of its DNA with PCR.

The present invention offers an objective method of screening, concentrating, characterizing, identifying, sequencing and/or cloning low levels of any organism or macromolecular entity which is capable of capture with a specific capture reagent and which also is capable of providing DNA for in vitro amplification.

DEFINITIONS

In order to provide a clear and consistent understanding of the specification and claims, including the scope to be given such terms, the following definitions are provided.

Macromolecular entity. The term "macromolecular entity" is intended to refer generally to any biological entity which is synthesized in, replicates in, or is extractable from, a biological source such as a microbe, plant, animal or the tissues thereof. Examples of macromolecular entities within the meaning of this word include infectious agents, bacteria, viruses, protozoans, pneumocystis, mycoplasma, parasites, fungi, molds, yeast or microbes. In some cases, a subcellular macromolecule or complex thereof may also be considered to be a macromolecular entity within the meaning of the invention. For example, a nucleic acid which is also antigenic, either due to the presence of a protein or other antigenic material bound to the nucleic acid, or to an inherent antigenicity in the nucleic acid itself and which allows it to be recognized by an antibody or other high affinity capture reagent, would be considered a macromolecular entity within the meaning of the invention.

Capture Reagent. The term "capture reagent" is intended to refer generally to a biological entity which has the inherent ability to bind to, and thus form an affinity with, a specific macromolecular entity. Capture reagents include polyclonal and monoclonal antibodies, receptor molecules, protein A, hormones, enzymes, desialylated glycoproteins, lectins, toxins, and the like. Organisms such as bacteria and viruses may, in certain instances, serve as capture reagents if they specifically interact with a unique target, such as a membrane receptor.

A virus or other organism may be used as a capture reagent to extract and concentrate cells or other macromolecular entities containing organism-specific receptors; the identity of the captured cell would then be determined by its genotype upon amplification of its DNA.

The type of organism or macromolecular entity which is capable of being extracted, concentrated, purified, characterized, cloned, identified or otherwise analyzed by the method of the invention is limited only by a) the identification of a specific capture reagent possessing an inherent affinity for and an ability to extract the macromolecular entity from the milieu in which it is found; and b) the identification of nucleic acid sequences which can be used to target specific sequences in the macromolecular entity for amplification.

The organism or macromolecular entity need only be nucleic acid-containing, not necessarily double-stranded (ds) DNA containing. Macromolecular entities that contain nucleic acid other than dsDNA, such as single-stranded (ss) RNA, ssDNA, dsRNA, or mRNA are capable of analysis by the method of the invention. For example, to amplify nucleic acid sequence information by PCR, which requires dsDNA, moieties containing nucleic add in a form other than dsDNA can be subjected to an intermediate step(s) in which the ssRNA, ssDNA, dsRNA or mRNA is converted to the dsDNA form.

For example, viruses containing ssDNA genomes can be converted to dsDNA with DNA polymerase I; viruses containing ss or dsRNA genomes can be converted to a dsDNA form by reaction with reverse transcriptase and DNA polymerase I. It is not necessary to transcribe the entire genome into dsDNA, rather the probes designed for use in the PCR can be used to prime the transcription of only a region of interest.

The use of reverse transcriptase and DNA polymerase I to synthesize dsDNA from ssRNA or ssDNA templates is well known in the art (Maniatis, T., et al, *Molecular Cloning (A Laboratory Manual)*, Cold Spring Harbor Laboratory, (1982)). This advantage has recently been recognized by others (Li. H. et al., *Nature* 335:414–417 (1988); and Mullis, K. B., EP201,184).

Alternatively, anti-sense RNA can be used to convert ssRNA to a ds form (Lichtenstein, C., *Nature* 333:801 (1988)).

In a preferred embodiment, the capture reagent used to extract the macromolecular entity is a monoclonal antibody, bound to a solid phase support. The sample is placed in contact with a monoclonal antibody on the solid phase support and the material, if desired, is incubated for a defined time, such as several hours or overnight. The desired time of incubation is that time required for affinity capture to be essentially complete. The temperature of this capture may be any temperature which permits affinity capture to occur in the desired time and is usually room temperature. The solid phase supports are then extensively washed with an appropriate physiological buffer, for example, a phosphate buffered saline solution at physiological pH, and the captured sample is used as a substrate for analysis with nucleic-acid amplification methodology.

In a preferred embodiment, the capture reagent bound to the solid phase support is used in the analysis of serum or other biological fluid or tissue for the presence of a pathogenic organism, eukaryotic cell or other macromolecular entity. The advantage of this method for the analysis of serum and other milieu which contain components inhibitory to PCR is that it isolates and concentrates the macromolecular entity, in a one step, highly specific manner from the milieu, leaving the macromolecular entity intact but sequestered, trapped and locatable on a matrix and amenable to other techniques.

In an illustrative preferred embodiment, high affinity monoclonal antibody 5D3 is bound to a solid phase and used to assay for the presence of hepatitis B antigen or its variants in serum. The cell line producing 5D3 was deposited with the American Type Culture Collection, 12301 Parklawn Drive, Rockville, Md. 20852, USA, on Aug. 25, 1988, and was assigned ATCC No. HB9801. Reference to antibody 5D3 is made in U.S. Pat. No. 4,271,145, issued to Wands, J. R., et al., as well as in Wands, J. R., et al., *Proc. Natl. Acad. Sci. USA* 78:1214–1218 (1981), both incorporated herein by reference.

As a first step in the invention, affinity capture of the organism or other macromolecular entity on a solid support is advantageous because it eliminates volume of the sample, or a dilute concentration of the macromolecular entity as being factors limiting the sensitivity of the invention. Affinity capture also eliminates the need for bulk in vitro extraction of DNA from serum samples or other samples containing inhibitors of the PCR prior to amplification analysis. The affinity capture step eliminates the need for preliminary growth, enrichment, or culture of samples to increase the number of organisms present to detectable levels. In addition, affinity selection provides a way to control the specificity of the analysis in a manner independent from the nucleic acid amplification and in a manner which does not necessarily adversely adulterate or otherwise harm the sample being tested. That is, by using affinity capture as a first step, the integrity of the non-extracted components in the sample is maintained. After affinity selection, the sample can be used in other assays.

The volume of a substance required for the analysis is a function of the affinity of the capture reagent for the organism or macromolecular entity to be captured and the expected concentration of the organism or macromolecular entity in the substance. The volume of the substance being tested for the presence of the macromolecular entity can be expanded to include any volume desirable, as long as the affinity capture reagent has access to that volume. Such access may be achieved, for example, by passing the volume of the substance being tested through a column containing the affinity capture reagent or through a filter containing the affinity capture reagent, or by passing a dipstick containing the bound capture reagent through a solution of the substance being tested.

The partial amino acid or nucleic acid sequence of the organism or macromolecular entity, however, must be known to prepare oligonucleotide primers or probes of defined sequences.

In another embodiment, the capture reagent is not bound to a solid phase support when it captures the organism or macromolecular entity, but is subsequently extracted and sequestered onto a solid phase, for example, by using filtration to deposit affinity-captured moieties on a filter, or by using a second affinity agent to recover the captured moieties, wherein the second affinity agent is bound to a solid phase.

The affinity capture reagent may be specific for one moiety in the sample or it may comprise a mixture of affinity reagents with differing specificity. Mixtures of affinity capture reagents may comprise: 1) mixtures wherein each reagent is directed to different affinity targets on the same moiety, or 2) mixtures wherein each affinity reagent is directed to a different moiety. In the latter example, the capture step would recover a group of different moieties in one step. Alternatively, the sample may be repeatedly exposed to a series of capture and extraction steps, each step extracting and isolating a different moiety in the sample.

Any appropriate geometry of the solid phase support, such as latex beads, membranes, dipsticks, microtiter dishes, and the like, can be used as the backbone upon which to present the capture reagent to the macromolecular entity.

The advantage of dipstick-bound capture reagents is that they can capture a macromolecular entity whether it is in solution or in a solid phase. For example, a dipstick can be passed through a solution. Alternatively, a dipstick may be placed in contact with the substance being tested, for example, by laying the dipstick on the top of a gel, blood smear, or tissue section.

In a preferred embodiment, the capture reagent is covalently bound to a bead and mixed with a solution containing the organism or macromolecular entity. After binding the entity, the beads are recovered by centrifugation and washed by resuspension and recentrifugation.

In another embodiment, affinity chromatography using high affinity monoclonal antibodies is utilized for the capture, purification and concentration of the macromolecular entity.

The source of the antibodies may be homologous with that of the macromolecular entity. For example, monoclonal antibodies to a hepatitis B virus envelope protein can be used for the extraction of any hepatitis B virus or variant that is present. Alternatively, the macromolecular entity may be heterologous to the source of the antibodies. For example, monoclonal antibodies to membrane proteins found in one type of cell can be used for the specific extraction of those cells. Cells sequestered in this manner can then be analyzed for the presence of a second entity, such as an integrated virus in said cells.

It is important that the affinity between the macromolecular entity and capture reagent be high enough to: 1) recognize and bind the macromolecular entity even in a very dilute biological milieu; and 2) withstand washing of the macromolecular entity-capture reagent complex to remove non-bound serum components.

Washing is accomplished by rinsing the solid phase-bound, macromolecular entity-capture reagent complex with an appropriate salt solution to promote the dissociation of components nonspecifically retained on the solid matrix, while maintaining the requestration, that is, interaction between the macromolecular entity and capture reagent.

Appropriate washing solutions include any solution which promotes dissociation of non-specifically bound substances while not promoting the dissociation of the specific complex between the capture reagent and the macromolecular entity. If the capture reagent is a high affinity monoclonal antibody, solutions such as 0.9% NaCl, phosphate-buffered saline, or even water, are appropriate.

The captured nucleic acid must be released from the bound organism or macromolecular entity and denatured before it can be used, amplified or otherwise analyzed. Nucleic acid liberated from the captured macromolecular entity by heating at a high temperature is used as a substrate for amplification and analysis.

In a preferred embodiment, the release of the captured DNA occurs concurrent with the first denaturation step in the PCR. For example, beads containing the captured organism are added directly to the PCR mixture. The sample is then heated to a temperature sufficient to both release DNA from the organism and to denature it, such as 94° C. for 1 minute and typically 80°–105° C. for 1–10 min. The remaining PCR steps are not altered. The sample is cooled to the desired annealing temperature for a time sufficient to allow the primers to anneal to the template, and then heated for the desired time at the temperature desired for the primer extension step. The temperature and time of annealing and extension are a function of primer composition and size and are well known to those in the art (See, e.g., Szostak, J. W., et al., *Meth. Enzymol.* 68:419–428 (1979); *Nucleic Acid Hybridization*, B. D. Hames and S. J. Higgins, eds., IRL Press, Washington, D.C., 1985; and Hamley, P. et al., *J. Biochem.* 254:4876 (1979)). Automated embodiments, capable of repeated cycles through the denaturing, annealing and extension temperatures, greatly simplify the procedure and are available as the "DNA thermocycler" from Perkin Elmer Cteus (Landegren, U., et al., *Science* 242:229–237 (1988)).

The primers can be prepared by any suitable method such as phosphotriester and phosphoester diester methodology (Mullis, K. B., EP 201,184; Beaucage, et al., *Tetrahedron Lett.* 22:1859–1862 (1981); and U.S. Pat. No. 4,458,066). The primer may be added to the reaction with a group of different primers, each designed to hybridize with a different target.

Methods for annealing and primer extension have been described (Cohen, S. N., U.S. Pat. No. 4,293,652; Erlich, H. A., et al., EP 258,017; Mullis, K. B., EP 201,184; Mullis, K. B., et al., EP 200362; Saiki, R. K., et al., *Science* 239:487–491 (1988); Mullis, K. B., et al., Meth. Enzymol. 155:335–350 (1987); Scharf, R. K., et al., *Science*

233:1076–1079 (1986) and Saiki, R. K., et al., *Science* 230:1350–1354 (1985)).

Extension of the template in the PCR is preferably performed with a heat stable polymerase, for example, the thermostat polymerase from *Thermus aquaticus* (Saiki, R. K., et al., EP258,017).

Methods to detect, analyze, sequence or clone the amplified macromolecular entity sequence include those conventional in the art of nucleic acid analysis, sequencing and cloning (Maniatis, T., et al., *Molecular Cloning* (A Laboratory Manual), Cold Spring Harbor Laboratory (1982); and Landegren, U., et al., *Science* 242:229–237 (1988)).

Detection methods include isotopic, fluorescent, chemiluminescent, immunoreactive or colormetric techniques.

For example, the amplified sequences may be labeled with a suitable radioactive label, including $^{32}P$, $^{3}H$, $^{14}C$, $^{35}S$, $^{125}I$, or the like. Any radioactive label may be employed which has a sufficiently long half-life. Transcribed regions may be radioactively labeled, for example, by "nick-translation" by well-known means, (e.g., Rigby, P. J. W., et al., *J. Mol. Biol.* 113:237 (1977)), or detected after hybridization to a radiolabelled probe.

Alternatively, the detection methodology may be based on detection of biotinated probes using alkaline phosphatase (Singer, R. H., et al., *BioTechniques* 4:230–249 (1986)), avidin and β-galaetosidase (Nagata, Y., et al., *FEBS Lett.* 183:379–382 (1985)), or aviden and biotin-specific antibodies (Ward, EP63,879).

The use of nucleic acid sequence information to detect or identify a moiety means the use of any technique which requires nucleic acid hybridization, for example with a primer or probe, to establish whether nucleic acid sequence similarity exists between the hybridizing nucleic add and the sample.

The sequence information contained in the amplified macromolecular entity can also be evaluated using conventional restriction enzyme techniques, gel chromatography or dot blot analysis.

The nucleic acid captured by the affinity matrix can be analyzed by any method sensitive enough to ultimately produce a detectable result (Landegren, U., et al., *Science* 242.:229–237 (1988)). For example, probes synthesized and amplified by Q-beta replicase methodology may be used to characterize the nucleic acid of the trapped sample, with or without previous amplification of the sample's nucleic acid by other means (Miele, E. A., et al., *J. Mol. Biol.* 1.71:281–295 (1983); Chu, B. C., *Nucl. Acids Res.* 14:5591–5603 (1986)). Other applicable technologies for the detection and analysis of the captured moiety's nucleic acid include the use of allele-specific nucleotide probes (Conner, B. J. et al., *Proc. Natl. Acad. Sci.* USA 80:278(1983)); the oligonucleotide ligation assay (Landegren, U., et al., *Science* 2.41:1077 (1988)); RNase A (Myers, R. M., et al., *Science* 230:1242 (1985)); denaturing gradient gels (Myers, R. M., et al., *Nature* 313:495 (1985)) and chemical cleavage (Cotton, R. G. H., et al., *Proc. Natl. Acad. Sci.* USA 85:4397 (1988)). The advantages and applications of these techniques have been recently reviewed (Landegren, U. et at, *Science* 242:229–237 (1988)).

An advantage of the method of the invention is that its specificity can be controlled at any one or combination of several steps: the affinity capture step; the nucleic acid amplification step; or the analysis step. For example, affinity capture using an antibody designed to capture all members of a certain class of virus can be coupled with nucleic acid amplification using primers or probes specific for a certain subclass of virus. Alternatively, primers or probes designed to amplify all members of a given class can be used and the identification of the subclass made on secondary characterization of the amplified nucleic acid, for example, by restriction enzyme analysis or sequencing.

The method of the invention is applicable to the detection and analysis of any virus such as hepatitis virus, picornavirus, retrovirus, reovirus, togavirus, orthomyxovirus, paramyxovirus, rhabdovirus, arenavirus, coronavirus, bunyavirus, papovirus, parvovirus, adenovirus, herpetovirus, or poxvirus, and especially hepatitis B, Non-A Non-B hepatitis virus, HIV-1, HIV-2, HTLV-1, HTLV-2, human papilloma virus, Epstein-Barr virus, or herpes simplex virus.

The method of the invention is also applicable to the detection of any species of bacteria such as *N. gonorrhea*, Chlamydia T., Candida A., *Pneumocystis carinii*, *E. coli* and the like.

The method of the invention is also applicable to the isolation and detection of low levels of malignant, transformed, tumorigenic or otherwise abnormal cells from biological fluids or tissues, especially, biopsy samples, where it would be desirable for an evaluation of the malignancy of a lesion or tissue for the patient's prognosis.

Examples of biological fluids, solids, or tissues assayable by the methods of the invention include serum, blood, blood cells, sputum, stool, saliva, urine, mucus, pus, warts, moles, and biopsy and tissue samples.

The method of the invention is especially useful for the monitoring of environmental air and water quality and the like, by placing a trap containing the capture reagent on a removable, replaceable solid phase, in-line with the air or water supply.

Having now generally described this invention, the same will be better understood by reference to certain examples which are included herein for purposes of illustration only and are not intended to be limiting unless otherwise specified.

EXAMPLE 1

RAPID DETECTION OF HEPATITIS B VIRUS AND ITS VARIANTS a) Preparation of the Capture Reagent Monoclonal antibody 5D3 has previously been characterized as being directed against the surface antigen of hepatitis B ($HB_sAg$) and as having an affinity constant for its antigenic determinant on $HB_sAg$ of $4\times10^{11}$ liters/mole per molecule (Wands, J. R., et al., *Gastroenterology* 80: 225–232 (1981)). Antibody 5D3 recognizes all known subtypes of $HB_sAg$ and by definition recognizes a part of the a domain of the virus (Ben-Porath, E., et al., *J. Clin. Invest.* 76:1338–1347 (1985)). The antibody was coupled to activated CNBr Sepharose beads at a protein concentration of 1 mg to 1 ml of Sepharose slurry (Ben-Porath, E., et al., in *Progress in Liver Diseases*, vol. VIII, (H. Popper and F. Shaftner, eds.), Grune & Stratton, New York, 1986, pp. 403–427; Marciniak, R., et al., *Proc. Natl. Acad. Sci.* USA 80:3214–3219 (1983)).

b) Incubation of the Capture Reagent with the Sample

Twenty-five microliters of Sepharose-coupled antibody slurry was added to 200 µl of serum and mixed overnight at 37° C. Serum was then decanted after a short centrifugation step. The antibody-Sepharose coupled beads were washed 6 times with phosphate buffered saline by suspension and repelleting to remove serum components from the antigen-antibody complex. The final Sepharose pellet which contains the bound HB$_s$Ag-associated particles, including virions with hepatitis B virus or its variants, was used directly in the PCR.

c) Selection of the DNA Probe Sequences

A computer analysis of known HBV DNA sequences was performed to search for regions of maximal homology representing functional and structural conservation, as well as significant heterogeneity suggesting evolutionary divergence. Careful selection of primer sequences was important because HBV strains from different parts of the world are known to contain significant heterogeneity (Tiollais, P., et al., *Nature* 317:489–495 (1985); Seeger, C., et al., *J. Virol.* 51:367–375 (1984)), and these HBV-related macromolecular entities may harbor DNA sequences significantly different from that of HBV.

A comparison of all the known DNA sequences of hepadenoviruses, including all the known HBV subtypes, ground squirrel hepatitis virus, (GSHV), woodchuck hepatitis virus (WHV), and duck hepatitis (DHV), was conducted for consensus sequences. Two stretches of nucleotides flanking the hepatitis core gene were identified that had remarkable conserved sequences. The first sequence is in the pre-core region and the other is in the 3' terminus of the core gene. The oligonucleotides representing these two regions are:

Oligo 1 (bases 1865–1889): 5'TTCAAGCCTCCAAGCTGTGCCT-TGG 3'

Oligo 2 (bases 2430–2410): 5'TCTGCGACGCGGCGATTGAGA 3'

PROBE (bases 1892–1916): 5'GGCTTTGGGGCATGGACAT-TGACCC 3'

The first nucleotide spans positions 1865 to 1889 (adw subtype), (Ben-Porath, E., et al., *J. Clin. Invest.* 76:1338–1347 (1985)). Its sequence is 100% conserved in the pre-core region of all known hepadenoviruses. The second oligonucleotide from position 2410 to 2430 also contains sequences which are generally conserved except in WHV and GSH which have a C to T transition at nucleotide position 2418 (Seeger, C., et al., *J. Virol* 51:367–375 (1984)). The third oligonucleotide from positions 2269 to 2288 between the two primers (oligo 1 and 2) is also well conserved and will be used as the probe for the amplified fragment. These two oligonucleotide primers will direct and amplify the synthesis of a 566-bp fragment in the PCR. The two oligonucleotide primers were synthesized using Applied Biosystem's DNA Synthesizer. The full-length oligonucleotides (25-mer for the first and 21-mer for the second oligonucleotide) were purified on preparative denaturing polyacrylamide gel electrophoresis away from shorter sequences which resulted from incomplete synthesis. The purified oligonucleotides have been shown to be homogeneous with the correct lengths free of other oligonucleotides on denaturing polyacrylamide gel. Preliminary results have shown that these two oligonucleotide primers bind specifically to the correct position on HBV DNA and are capable of directing DNA synthesis in the PCR.

Other sequences of homology in the HBV genome have been examined and several oligonucleotide primers in other regions of interest, such as in the pre-S and S domains, have been selected. By comparison of available nucleotide sequences from different HBV subtypes (adw, adr, ayw) different sets of conserved DNA sequences to be used as primers can be defined. Each primer carries a restriction enzyme site at its 5' end for subsequent cloning.

The nucleotide sequences of five sets of the selected primers spanning the entire S region and cloning sites (sequences in bold faced type are mismatched and the underlined sequences are the restriction enzyme sites) are presented below:

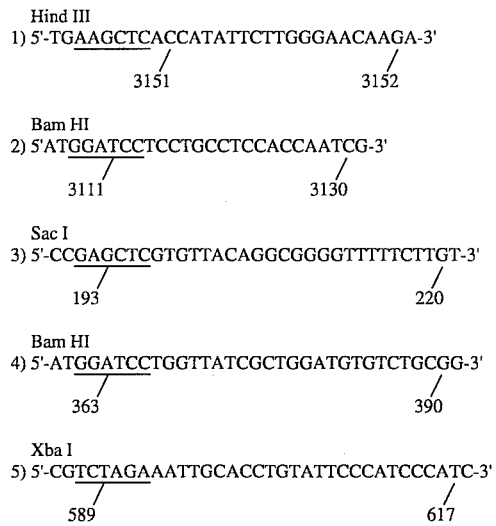

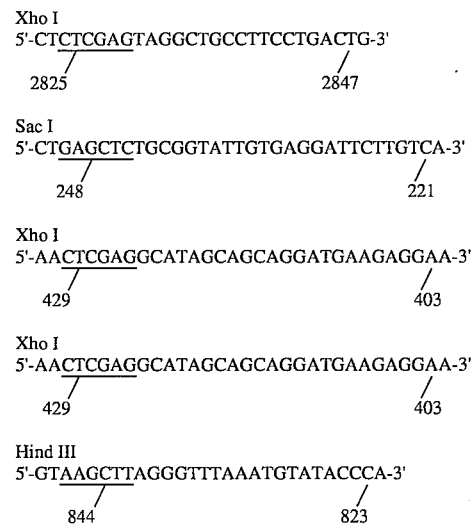

d) Use of the Probes in PCR to Amplify Captured HBV and/or Variant DNA Sequences The viral particles must first be denatured to expose their DNA to the primers. This is accomplished by running the initial PCR step at a minimum of 80° C.

Amplification of DNA sequences using the PCR and heat-stable polymerase from Thermus Aquaticus (Taq polymerase) has been described elsewhere (Chien, A. et al., *J. Bacteriol* 127:1550–1557 (1976); Saiki, R. K., et al., *Science* 230:1350–1354 (1988)). The method is a modification of the procedure described by Saiki, supra. DNA was amplified in a 50 µl reaction volume containing 25 pmole of each oligonucleotide primer in 1×reaction buffer [10 mM Tris-Cl pH 8.3, 50 mM KCl, 1.5 mM MgCl$_2$, 0.01% (w/v) gelatin, 200 mM of dATP, dGTP, dCTP, TTP each and 0.25 units of Taq polymerase (Cetus)]. Reaction mixtures were overlaid with 30 μl of mineral oil to prevent evaporation. Samples were heated at 94° C. for 1 minute to denature the DNA, placed at 45° C. for 2 minutes to allow primers to anneal to the template, then transferred to 72° C. for 3 minutes for primer-directed DNA synthesis. Subsequent rounds consisted of repeated cycles of the denaturing step described above at 95° C., cool-down at 45° C. and an extension step at 72° C. On the average, 25 to 35 rounds were performed in this manner. The amplified samples were analyzed either by direct spotting of an aliquot to nylon membrane for DNA dot-blot hybridization or on agarose gel to visualize the amplified fragments by ultraviolet light fluorescence after staining with ethidium bromide, or, by direct probing with a subgenomic fragment of HBV-DNA or by a defined oligonucleotide sequence within the amplified DNA (see below).

e) Comparison of the Sensitivity of Hepatitis B Virus Detection using only the PCR or using Monoclonal Antibody Capture plus PCR.

Figure 1B:
Figure 2:
FIG. 2 is a Southern analysis showing the sensitivity of the combination of monoclonal antibody capture and 35-cycle polymerase chain amplification as compared to immunoassay by the M-IRMA technique. The dilution of the serum and the results of the M-IRMA analysis are placed at the top of each lane. Lanes 1 and 2 represent standards used for molecular weight markers.

As is shown in FIG. 1, using only PCR to detect hepatitis B virus in a serum sample, the sensitivity of detecting a 566 bp transcript following 25 rounds of amplification was $10^{-5}$ pg HBV DNA by hybridization; (it was only $10^{-2}$ pg HBV DNA by ethidium bromide staining of agarose gels). It is noteworthy that $10^{-5}$ pg of HBV DNA corresponds to 3 molecules of HBV genome. Continuing the PCR beyond 25 cycles will amplify DNA even further; $10^{-5}$ pg of HBV DNA can be detected by ethidium bromide staining after 35 rounds of PCR, reflecting an amplification magnitude of $>10^9$. FIG. 2 demonstrates the sensitivity of the monoclonal antibody capture system when it is combined with the PCR. Serum from a patient who was reactive by both the M-IRMA immunoassay (Ben-Porath, E. supra) and DNA hybridization (dot blot technique) was serially diluted. Binding of the monoclonal M-IRMA assay was compared to the PCR assay following capture with the monoclonal anti-HBS IgM linked to a solid phase support. A positive result in the M-IRMA assay is a S/N value of greater than 2. As is shown in FIG. 2, at a dilution between $10^{-4}$ and $10^{-5}$ the M-IRMA becomes negative. However, by the technique of the invention, that is, by using PCR to amplify the DNA captured by the monoclonal antibody, a serum dilution of $10^{-7}$ is easily detectable. This indicates that the combination of antibody capture with the PCR amplification step is approximately 1000-fold more sensitive than the immunoassay for the detection of the hepatitis B virus or its variants in serum from a patient.

f) Detection of Hepatitis B Virus DNA Sequences By Monoclonal Antibody IgM Capture followed by PCR Amplification in Patients with Chronic Liver Disease Patients were examined who had been diagnosed as having chronic liver disease but in whom conventional hepatitis B virus marker (anti-HBcAG, anti-HB$_s$Ag and HG$_s$Ag) was not detected by commercial assay (AUSAB, CORAB, and AUSRIA II, Abbott Laboratories). Two patients who did test positive by commercial assays for one of the markers were also examined: patient number 11 tested positive for anti-HBcAG and patient number 12 tested positive for anti-HB$_s$Ag. The serum from all patients was tested by dot blot hybridization against a hepatitis B virus probe and found to be negative. The serum from all patients was also tested by immunoassay (Ben-Porath, E., supra), for the presence of HB$_s$Ag associated epitopes by M-IRMA.

Figure 3:
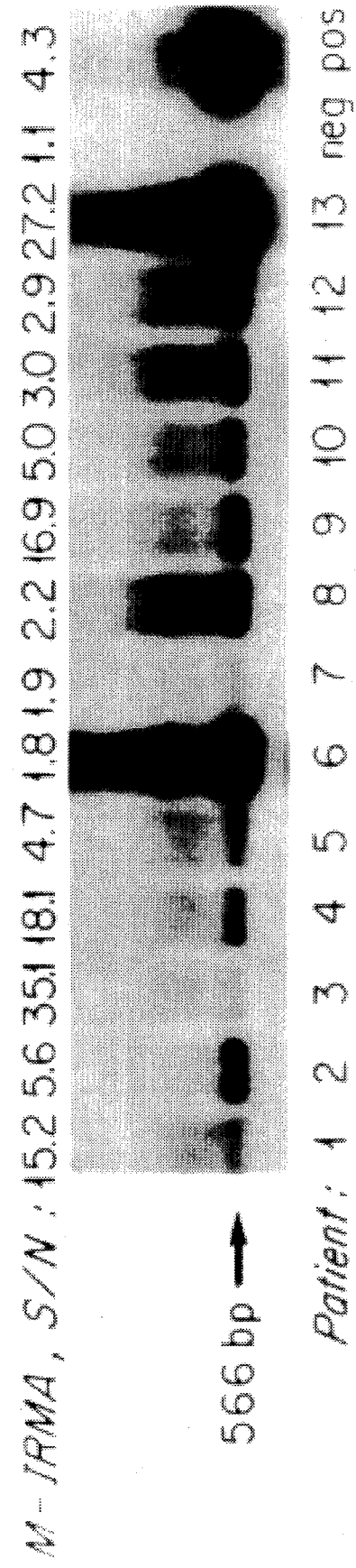
FIG. 3 shows the detection of hepatitis B virus DNA sequences in patients with chronic liver disease.
Figure 4:
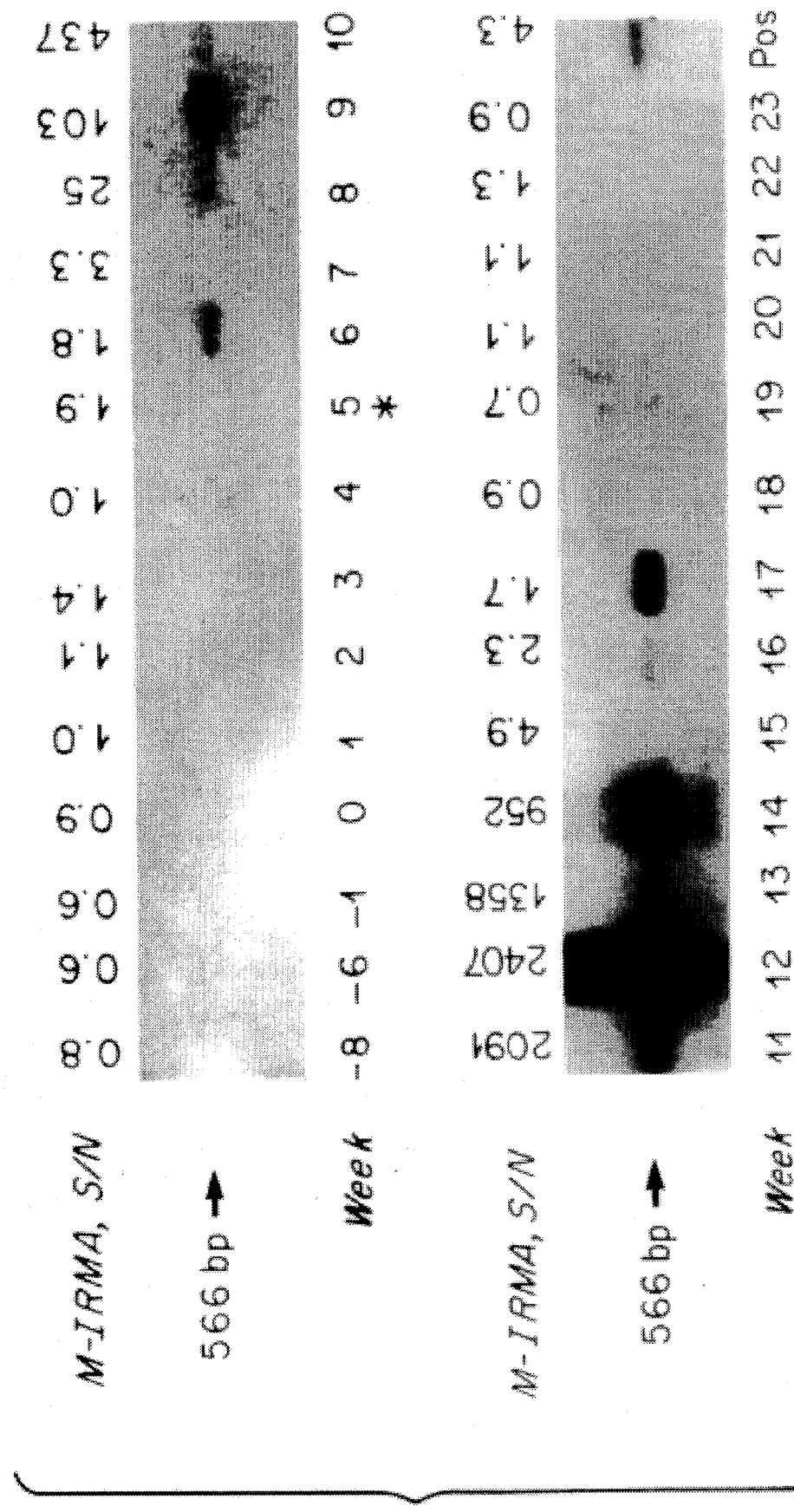
FIG. 4 shows the detection of hepatitis B virus DNA sequences in a chimpanzee inoculated with serum derived from a patient tentatively diagnosed as having chronic, Non-A Non-B hepatitis.

FIG. 3 shows the results of the M-IRMA assay and the capture/amplification assay. Amplified DNA was electrophoresed on agarose gels, transferred to nylon membranes and hybridized with $^{32}$P-hepatitis B virus DNA. The last two lanes in the figure represent negative and positive controls, respectively. As shown in FIG. 3, all of the patients were clearly identified as being hepatitis B carriers by the method of the invention. Some of these patients, for example patients Nos. 6 and 7, had been missed by the M-IRMA assay.

g) Detection of Hepatitis B Virus DNA by Monoclonal Antibody Capture Followed by Polymerase Chain Amplification in a Chimpanzee Undergoing Experimental Infectivity Studies with Hepatitis B Virus A chimpanzee was inoculated with serum derived from a patient with presumed chronic, Non-A Non-B hepatitis (patient number 9 in FIG. 3). This patient's serum was reactive for HB$_s$Ag-associated epitopes only by M-IRMA and was negative for all other hepatitis B virus associated serologic markers. The chimpanzee was bled weekly and his serum analyzed for HB$_s$Ag associated epitopes by M-IRMA and for hepatitis B virus sequences by monoclonal anti-HBs IgM capture followed by polymerase chain amplification. As is shown in FIG. 4, the method of the invention detected the virus in the chimp's serum before it was detected by either M-IRMA or by hepatitis B virus DNA hybridization by dot blot techniques.

During these experimental infectivity studies in a chimpanzee, hepatitis B virus DNA was detected by the monoclonal capture technique of the invention four weeks after inoculation. This was earlier than the appearance of the HB$_s$Ag marker as detected by M-IRMA. Even in the presence of low titer anti-HBs at week 17, hepatitis B virus DNA was still detectable in serum by the method of the invention. Importantly, hepatitis B virus was still being detected by the method of the invention after clearance of the virus had been indicated by the M-IRMA technique. This indicates that hepatitis B virus remains in the blood for a longer period of time than previously recognized. These results demonstrate that this technique is much more sensitive for the detection of virus than either M-IRMA or dot blot analysis.

h) Cloning of DNA Captured by the Antibody-Amplification Technique

After 35 cycles of amplification, enough DNA is available for digestion and cloning with appropriate restriction enzymes. The amplified DNA sequences can be cloned in TG1 bacteria after insertion in bacteriophage $M_{13}$mp18 and $M_{13}$mp19 to obtain both orientations of the insert. The phage containing recombinants can be detected using an internal oligonucleotide as a probe. Single stranded M13 recombinant DNA will be prepared and sequencing performed using the dideoxy extension method.

Now having fully described this invention, it will be understood by those with skill in the art that the scope may be performed within a wide and equivalent range of conditions, parameters, and the like, without affecting the spirit or scope of the invention or of any embodiment thereof.

What is claimed is:

1. A method for the detection or identification of an antigenic, nucleic acid-containing virus present at dilute level in a biological sample, wherein said virus is selected from the group consisting of hepatitis virus, picornavirus, retrovirus, reovirus, togavirus, orthomyxovirus, paramyxovirus, rhabdovirus, arenavirus, coronavirus, bunyavirus, papovirus, parvovirus, adenovirus, herpetovirus, and poxvirus, which comprises the steps of:
   a. affinity capturing whole virus from said biological sample being tested, thereby concentrating said whole virus;
   b. denaturing said whole virus to yield a mixture of antigen and nucleic acid; and
   c. directly amplifying denatured nucleic acid sequences specific to said virus present in said mixture, thereby detecting or identifying said virus.

2. The method of claim 1, wherein said virus is hepatitis B, Non-A Non-B hepatitis virus, HIV-1, HIV-2, HTLV-1, HTLV-2, human papilloma virus, Epstein-Barr virus or Herpes Simplex Virus.

3. A method for the detection or identification of an antigenic, nucleic acid-containing macromolecular entity present at a dilute level in a biological sample which comprises the steps of:
   a. affinity capturing whole macromolecular entity from said biological sample being tested, thereby concentrating said whole macromolecular entity wherein said biological sample is selected from the group consisting of foodstuff, grain, soil, water, air, sputum, stool, saliva, urine, mucus, pus, warts, moles, biopsy samples and tissue samples;
   b. denaturing said whole macromolecular entity to yield a mixture of antigen and nucleic acid; and
   c. directly amplifying denatured nucleic acid sequences specific to said macromolecular entity present in said mixture, thereby detecting or identifying said macromolecular entity.

* * * * *